(12) United States Patent
Wang et al.

(10) Patent No.: US 11,039,762 B2
(45) Date of Patent: Jun. 22, 2021

(54) JOINT MOVEMENT ANALYSIS SYSTEM AND METHOD; KNEE-JOINT DYNAMIC EVALUATION METHOD AND SYSTEM

(71) Applicant: INNOMOTION INCORPORATION (SHANGHAI), Shanghai (CN)

(72) Inventors: Shaobai Wang, Shanghai (CN); Fang Sun, Shanghai (CN); Hui Wang, Shanghai (CN)

(73) Assignee: INNOMOTION INCORPORATION (SHANGHAI), Shanghai (CN)

(*) Notice: Subject to any disclaimer, the term of this patent is extended or adjusted under 35 U.S.C. 154(b) by 407 days.

(21) Appl. No.: 15/774,810

(22) PCT Filed: Apr. 25, 2016

(86) PCT No.: PCT/CN2016/080115
§ 371 (c)(1),
(2) Date: May 9, 2018

(87) PCT Pub. No.: WO2017/080137
PCT Pub. Date: May 18, 2017

(65) Prior Publication Data
US 2018/0333084 A1 Nov. 22, 2018

(30) Foreign Application Priority Data

Nov. 13, 2015 (CN) .......................... 201510778570.8
Apr. 8, 2016 (CN) .......................... 201610216324.8

(51) Int. Cl.
*A61B 5/11* (2006.01)
*G16H 50/50* (2018.01)
(Continued)

(52) U.S. Cl.
CPC .......... *A61B 5/1127* (2013.01); *A61B 5/0075* (2013.01); *A61B 5/1121* (2013.01);
(Continued)

(58) Field of Classification Search
CPC ..... A61B 5/1127; A61B 90/39; A61B 5/0075; A61B 5/1121; A61B 5/4528; A61B 2090/397; A61B 2560/0223; G16H 50/50
(Continued)

(56) References Cited

U.S. PATENT DOCUMENTS

2007/0275830 A1    11/2007  Lee et al.
2008/0161731 A1     7/2008  Woods et al.
2016/0270696 A1*    9/2016  Lang .................... A61B 5/4585

FOREIGN PATENT DOCUMENTS

CN       1748642 A    3/2006
CN     101627900 A    1/2010
(Continued)

OTHER PUBLICATIONS

Favre, Julien, et al. "Functional calibration procedure for 3D knee joint angle description using inertial sensors." Journal of biomechanics 42.14 (2009): 2330-2335. (Year: 2009).*
(Continued)

*Primary Examiner* — David J. McCrosky
*Assistant Examiner* — Chanel J Jhin
(74) *Attorney, Agent, or Firm* — Muncy, Geissler, Olds & Lowe, P.C.

(57) ABSTRACT

A knee joint dynamic evaluation method for diagnosing human joint diseases by tracking motions of the knee joint includes constructing an evaluation model including a first angular difference threshold α1, a second angular difference threshold α2, and an anterior-posterior displacement difference threshold ε; synchronously collecting a single set of three-dimensional and six-degree-of-freedom movement data of a left knee joint and that of a right knee joint with devices; comparing the three-dimensional and six-degree-of-freedom movement data between the left and right knee joints with a data analyzing device, and calculating differ-
(Continued)

S1: setting actual marker points at a set position around the joint and virtual marker points at an anatomical bony structure landmark positions of the joint by a calibrating device, the space position of the actual marker points can track the space movement of the bony structure of the joint, to establish a relative space positions of the virtual marker points and the actual marker points;

S2: sensing the space position of the actual marker points by an optical tracking device so as to obtain space movement data of the actual marker points;

S3: collecting the space movement data of the actual marker points and relative position data of the virtual marker point and the actual marker point;

S4: obtaining the space movement data of the virtual marker points through the optimization operation of the space movement data of the actual marker points, and simulating and analyzing the movement condition of the joint bony structure according to the space movement data of the virtual marker points.

ences of the flexion and extension angles, the medial and lateral tilt angles, the medial and lateral rotation angles, and the anterior-posterior displacement movement values of the two sets of movement data; inputting the differences into the evaluation model to obtain the corresponding grading system, which will output the first, second, third, or fourth evaluation level.

9 Claims, 4 Drawing Sheets

(51) Int. Cl.
*A61B 90/00* (2016.01)
*A61B 5/00* (2006.01)

(52) U.S. Cl.
CPC ............ *A61B 5/4528* (2013.01); *A61B 90/39* (2016.02); *G16H 50/50* (2018.01); *A61B 2090/397* (2016.02); *A61B 2560/0223* (2013.01)

(58) Field of Classification Search
USPC ........................................................ 600/595
See application file for complete search history.

(56) References Cited

FOREIGN PATENT DOCUMENTS

| | | |
|---|---|---|
| CN | 104274182 A | 1/2015 |
| CN | 204293162 U | 4/2015 |
| CN | 105468896 A | 4/2016 |

OTHER PUBLICATIONS

Wu, Wenge et al., "A New Measuring Analyser for Knee Joint Function and Its Usage and Evaluation Method", Modern Rehabilitation, Oct. 2001, 1 page, vol. 5, No. 10.

* cited by examiner

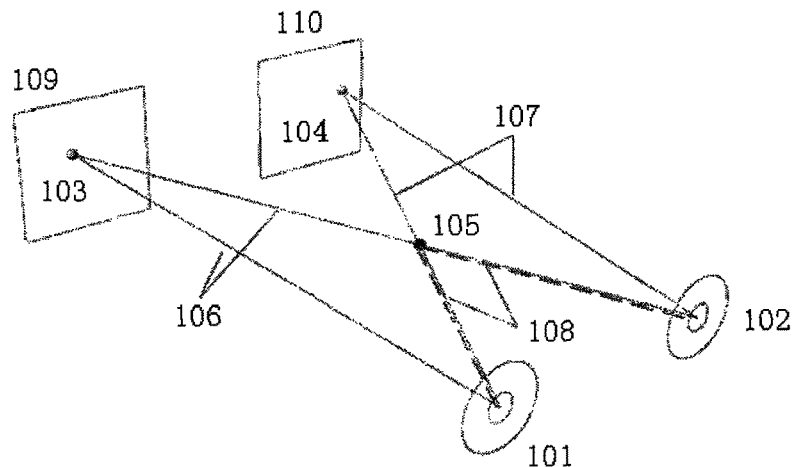

Fig.3

T1: constructing an evaluation model which includes at least a first angular difference threshold ¦ Åand a second angular difference threshold ¦ Åfor determining the movement angular differences, and an anterior-posterior displacement difference threshold ¦ Åor determining an anterior-posterior displacement movement difference, and a grading system according to these thresholds;

T2: synchronously collecting a single set of three-dimensional and six-degree-of-freedom movement data of the left knee joint and that of the right knee joint, each set of three-dimensional and six-degree-of-freedom movement data includes at least a flexion/extension angle, a medial and lateral tilt angle, and a medial and lateral rotation angle and an anterior-posterior displacement movement value;

T3: comparing the three-dimensional and six-degree-of-freedom movement data between the left and right knee joints, and calculating the differences of the flexion and extension angle, the medial and lateral tilt angles, the medial and lateral rotation angles, and the anterior-posterior displacement movement values of the two sets of data;

T4: inputting the differences into the evaluation model to obtain a corresponding grading system.

Fig.4

JOINT MOVEMENT ANALYSIS SYSTEM AND METHOD; KNEE-JOINT DYNAMIC EVALUATION METHOD AND SYSTEM

TECHNICAL FIELD

The invention belongs to the field of signal detection and processing, and in particular relates to a joint movement analysis system and method.

BACKGROUND ART

It is necessary to understand a joint movement in many fields, for example, in the fields of bionics, medicine, etc. to establish a bionic model by understanding the joint movement, to design the other bionic devices, or diagnose the joint by observing the joint movement in the field of medicine. Especially for the movement of human joints, such as knee, ankle, hip, wrist, elbow and shoulder, the analysis and evaluation of the movement of these joints have great significance.

The traditional medical joint analysis methods are static analysis methods, such as magnetic resonance imaging (MM), X-ray imaging (X-ray), spiral tomography (CT) and other imaging analysis methods. The analysis result is a static image and cannot track the joint movement and abnormal results caused by joint movement. There is also a manual test, such as a drawer test and a lachman test (an anterior drawer test with a knee bend of 30°). The test results are subjective and qualitative based on externally imposed motions, and can not quantitatively track a actual movement of the joint. All of the above methods can not detect and analyze the movement of the joint dynamically and objectively.

There are currently large-scale gait labs capturing the joint motion with multiple motion capture cameras. However, the multiple cameras must be systematically calibrated before testing, and a large floor space is required for equipment placement, so the analysis is very inconvenient.

CONTENTS OF THE INVENTION

The technical problem to be solved by the present invention is to provide a joint motion analysis system and method capable of dynamically detecting the movement of the joint, and the analysis result can track the actual condition of the joint more accurately.

To solve the problem said above, the invention provides a joint movement analysis system, comprising:
a calibrating device which is used for setting actual marker points at a set position around a joint and virtual marker points at anatomical bony landmark positions of the joint, the space position of the actual marker points can track the space movement of the bony structure of the joint, and for establishing the relative space position of the virtual marker points and the actual marker points; an optical tracking device which is used for tracking the space position of the actual marker points so as to obtain a space movement data of the actual marker points;
a data collection device which is used for collecting the space movement data of the actual marker points and a relative space position data of the virtual marker points and the actual marker points; a data analyzing device which is used for obtaining the space movement data of the virtual marker points by optimization operating of the movement data of the actual marker points, and simulating and analyzing the movement condition of the bony structure of the joint according to the space movement data of the virtual marker points.

According to an embodiment of the present invention, the data collection device obtains the space movement data of the virtual marker points by optimization operation of the space movement data of the actual marker points under the condition that a geometric relationship between the actual marker points and the virtual marker points remains substantially unchanged or changes negligibly during the joint movement.

According to an embodiment of the present invention, the calibrating device includes at least two actual marking element groups used for calibrating the actual marker points. Each actual marking element group comprises at least four marking elements. The relative position between the marking elements remains substantially unchanged or changes negligibly during the joint movement.

According to an embodiment of the present invention, the calibrating device includes at least one set of special marking element group used for marking the virtual marker points. The optical tracking device can sense all of the actual marking element groups and special marking elements groups synchronously at least one time so as to determine the relative space position of the actual marker points and the virtual marker points.

According to an embodiment of the present invention, according to the characteristic that a distance from any three marking elements used for marking the actual marker points to the virtual marker points which has been marked remains substantially unchanged or changes negligibly during the joint movement, the data analyzing device determines the space position of the virtual marker points selected in any frame of the joint movement sensed by the optical tracking device according to the object of optimization that the distance from the virtual marker points to the three actual marker points is approach the distance from the virtual marker points to the three actual marker points in original positions, and obtains the space movement data of the virtual marker points.

According to an embodiment of the present invention, the data analyzing device simulates and analyzes the three-dimensional and six-degree-of-freedom movement data of the joint according to the displacement of the space movement data of the virtual marker points along the anatomical coordinate system of the joint and the rotation around the anatomical coordinate system of the joint.

According to an embodiment of the present invention, a database model is further included for storing normal human joint movement data; the data analyzing device is also used for comparing the acquired three-dimensional and six-degree-of-freedom movement data of a joint and that of the normal human joints.

According to an embodiment of the present invention, the calibrating device is an elastic binding device or a convenient attachment device for binding or attaching the actual marker points at a set position around a joint to establish a relative position of the virtual marker points and the actual marker points through a characteristic calibration pointer.

According to an embodiment of the present invention, the optical tracking device is an infrared sensing device, and the actual marker points of the calibrating device is an object that can be sensed by the infrared sensing device.

According to an embodiment of the present invention, the optical tracking device synchronously acquires a plurality of actual marker points.

According to an embodiment of the present invention, the optical tracking device is a dual infrared or multi-infrared integrated optical positioning sensor which determines the space position of the actual marker points by the time difference between infrared emission and reflection or the time difference of infrared light reception so as to obtain the space movement data of the actual marker points.

The present invention further provides a joint movement analysis method comprising the following steps:

S1: setting actual marker points at a set position around a joint and virtual marker points at anatomical bony landmark positions of the joint by a calibrating device, the space position of the actual marker points can track the space movement of the bony structure of the joint, to establish a relative space positions of the virtual marker points and the actual marker points;

S2: sensing the space position of the actual marker points by an optical tracking device so as to obtain a space movement data of the actual marker points;

S3: collecting the space movement data of the actual marker points and a relative position data of the virtual marker points and the actual marker points;

S4: obtaining a space movement data of the virtual marker points through the optimization operation of the space movement data of the actual marker points, and simulating and analyzing the movement condition of the bony structure of the joint according to the space movement data of the virtual marker points.

According to an embodiment of the present invention, the calibrating device includes at least two actual marking element groups used for calibrating the actual marker points. Each actual marking element group comprises at least four marking elements; a relative position between the marking elements remains substantially unchanged or changes negligibly during the joint movement.

According to an embodiment of the present invention, the said calibrating device includes at least one set of special marking element group used for marking the virtual marker points. The optical tracking device can sense all of the actual marking element groups and special marking element groups synchronously at least one time so as to determine the relative space position of the actual marker points and the virtual marker points.

According to an embodiment of the present invention, in the step S3, according to the characteristic that a distance from any three marking elements used for marking the actual marker points to virtual marker points which has been marked remains substantially unchanged or changes negligibly during the joint movement, the data analyzing device determines the space position of the virtual marker points selected in any frame of the joint movement sensed by the optical tracking device according to the object of optimization that the distance from the virtual marker points to three actual marker points is approach the distance from the virtual to the three actual marker points in original position, and obtains the space movement data of the virtual marker points.

According to an embodiment of the present invention, in the step S3, obtaining the space movement data of the virtual marker points by optimization operation of the space movement data of the actual marker points under the condition that a geometric relationship between the actual marker points and the virtual marker points remains substantially unchanged or changes negligibly during the joint movement.

According to an embodiment of the present invention, a step S5 if further included after the step S4, in this step, simulating and analyzing the three-dimensional and six-degree-of-freedom movement data of the joint according to the displacement of the space movement data of the virtual marker points along the anatomical coordinate system of the joint and the rotation around the anatomical coordinate system of the joint.

According to an embodiment of the present invention, in the step S2, the space position of the actual marker points are determined by at least two optical positioning sensors according to the time difference between infrared emission and reflection or the time difference of infrared light reception so as to obtain the space movement data of the actual marker points; the relative space position of the virtual marker points and the actual marker points is established by sensing the space position of the actual marker points and virtual marker points at least one time.

According to an embodiment of the present invention, in the step S2, calculating the distance from each marker points relative to other marker points for each frame of imagine, and sorting the distance; comparing the back frame with the front frame, to search for each marker points based on minimum distance errors, and to make marker points in the back frame correspond to that in the front frame.

The present invention further provides a knee joint dynamic evaluation method comprising the following steps:

T1: constructing an evaluation model which includes at least a first angular difference threshold $\alpha 1$ and a second angular difference threshold $\alpha 2$ for determining a movement angular difference, and an anterior-posterior displacement difference threshold $\varepsilon$ for determining an anterior-posterior displacement movement difference, and a grading system according to these thresholds;

T2: synchronously collecting a single set of three-dimensional and six-degree-of-freedom movement data of a left knee joint and that of a right knee joint, each set of three-dimensional and six-degree-of-freedom movement data includes at least a flexion/extension angle, a medial and lateral tilt angle, a medial and lateral rotation angle and an anterior-posterior displacement movement value;

T3: comparing the three-dimensional and six-degree-of-freedom movement data of the left and right knee joints, and calculating the differences of the flexion and extension angles, the medial and lateral tilt angles, the internal and medial and lateral angles, and the anterior-posterior displacement movement values of the two sets of movements;

T4: inputting the differences into the evaluation model to obtain a corresponding grading system; if all three angular differences are smaller than the first angular difference threshold $\alpha 1$ and the anterior-posterior displacement movement difference value is smaller than the anterior-posterior displacement difference threshold $\varepsilon$, then the evaluation model outputs a first evaluation level; if at least one angular difference is within the closed interval formed by the first angular difference threshold $\alpha 1$ and the second angular difference threshold $\alpha 2$, and the anterior-posterior displacement movement difference value is smaller than the anterior-posterior displacement difference threshold $\varepsilon$, then the evaluation model outputs a second evaluation level; if at least one angular difference is greater than or equal to the second angular difference threshold $\alpha 2$ and the anterior-posterior displacement movement difference value is smaller than the anterior-posterior displacement difference threshold $\varepsilon$, or all three angular differences are smaller than the second angular difference threshold $\alpha 2$ and the anterior-posterior displacement movement difference value is greater than or equal to the anterior-posterior displacement difference threshold $\varepsilon$, the evaluation model outputs a third evaluation level; if at least two angular differences are greater than or equal to the second angular difference threshold α2, or at least one angular difference is greater than or equal to the second angular difference threshold α2 and the anterior-posterior displacement movement difference value is greater than or equal to the anterior-posterior displacement difference threshold ε, then the evaluation model outputs a fourth evaluation level.

According to an embodiment of the present invention, the first angular difference threshold α1 is in a range of 3 to 7 degrees, and the second angular difference threshold α2 is in a range of 8 to 12 degrees. The anterior-posterior displacement difference threshold ε is in a range of 1 to 2 cm.

According to an embodiment of the present invention, the first angular difference threshold α1 is 5 degrees, and the second angular difference threshold α2 is 10 degrees. The anterior-posterior displacement difference threshold ε is 1.5 cm.

According to an embodiment of the present invention, in the step T2, respectively and synchronously multi-cycle collecting the three-dimensional and six-degree-of freedom movement data of the left and right knee joint in a certain period of time, obtaining a single set of three-dimensional six-degree-of-freedom movement data for the left knee and a single set of three-dimensional six-degree-of-freedom movement data for the right knee by numerical statistics of the multi-cycle collected three-dimensional six-degree-of-freedom movement data.

According to an embodiment of the present invention, the step of collecting three-dimensional six-degree-of-freedom motion data includes the following steps:

T21: setting actual marker points above and below left and right knee joints and setting virtual marker points at anatomical bony landmark positions of the knee joint, and calibrating the actual marker points and the virtual marker points by the calibrating device.

T22: respectively determining a relative position relationship between the actual marker points and the virtual marker points of the left and right knee joints by identifying the calibrating device with a mark recognition device, T23: after the relative position relationship being determined, identifying the calibrating device of the actual marker points for multiple times by the mark recognition device during the knee joint movement within a certain time, so as to obtain the space movement data of the actual marker points, then obtaining or optimizing the space movement data of the virtual marker points according to the relative position relationship and the space movement data of the actual marker points.

T24: constructing the three-dimensional and six-degrees-of-freedom movement data of the left and right knee joints by the displacement of the space movement data of the virtual marker points along the anatomical coordinate system of the joint and the rotation around the anatomical coordinate system of the joint.

According to an embodiment of the present invention, the calibrating device includes at least two actual marking element groups used for calibrating the actual marker points. Each actual marking element group comprises at least four marking elements. A relative position between the marking elements remains substantially unchanged or changes negligibly during the knee joint movement.

According to an embodiment of the present invention, the calibrating device includes at least one set of special marking element group used for marking the virtual marker points; in the step T22, the mark recognition device can synchronously sense all of the actual marking element groups and special marking element groups at least in one time so as to determine the relative position relationship of the actual marker points and the virtual marker points.

According to an embodiment of the present invention, in step T23, according to the characteristic that the distance from any three marking elements used for marking the actual marker points to the virtual marker points which has been marked remains substantially unchanged or changes negligibly during the knee joint movement, the mark recognition device determines the space position of the virtual marker points selected in any frame of knee joint movement sensed by the mark recognition device according to the object of optimization that the distance from the virtual marker points to the three actual marker points is approach the distance from the virtual to the three actual marker points in original position, and obtains the space movement data of the virtual marker points.

The present invention further provides a knee joint dynamic assessment system, comprising: a model constructing module which is used for constructing an evaluation model, the evaluation model includes at least a first angular difference threshold α1 and a second angular difference threshold α2 for determining the movement angular difference, and an anterior-posterior displacement difference threshold ε for determining the anterior-posterior displacement movement difference, and a grading system according to these thresholds;

a data collection module is used for synchronously collecting a single set of three-dimensional and six-degree-of-freedom movement data of the left knee joint and that of the right knee joint, each set of three-dimensional and six-degree-of-freedom movement data includes at least a flexion/extension angle, a medial and lateral tilt angle, and a medial and lateral rotation angle and a anterior-posterior displacement movement value;

a comparison module which is used for comparing the three-dimensional and six-degree-of-freedom movement data of the left and right knee joints and calculating the difference between the flexion and extension angles, the medial and lateral tilt angles, the medial and lateral rotation angles, and the anterior-posterior displacement movement values of the two sets of data;

a classification output module which is used for obtaining the evaluation model and inputting the differences into the evaluation model to obtain a corresponding grading system; if all three angular differences are smaller than the first angular difference threshold α1 and the anterior-posterior displacement movement difference value is smaller than the anterior-posterior displacement difference threshold ε, then the evaluation model outputs a first evaluation level; if at least one angular difference is within the closed interval formed by the first angular difference threshold α1 and the second angular difference threshold α2, and the anterior-posterior displacement movement difference value is smaller than the anterior-posterior displacement difference threshold ε, then the evaluation model outputs a second evaluation level; if at least one angular difference is greater than or equal to the second angular difference threshold α2 and the anterior-posterior displacement movement difference value is smaller than the anterior-posterior displacement difference threshold ε, or all three angular differences are smaller than the second angular difference threshold α2 and the anterior-posterior displacement movement difference value is greater than or equal to ε, the evaluation model outputs a third evaluation level; if at least two angular differences are greater than or equal to the second angular difference threshold α2, or at least one angular difference is greater than or equal to the second angular difference threshold α2 and the anterior-posterior displacement movement difference value is greater than or equal to the anterior-posterior displacement difference threshold ε, then the evaluation model outputs a fourth evaluation level.

According to an embodiment of the present invention, setting the actual marker points above and below left and right knee joints and setting the virtual marker points at anatomical bony landmark positions of the knee joint, and calibrating the actual marker points and the virtual marker points by the calibrating device; the data collection module includes:

a calibration data receiving unit which is used for receiving the first set of data obtained by the mark recognition device identifying all calibrating devices, or the second set of data obtained by the mark recognition device multiply identifying the calibrating devices for actual marker points during the knee joint movement;

a position relationship establishing unit which is used for determining a relative position relationship between the actual marker points and the virtual marker points of the left and right knee joints according to the first set of data received by the calibration data receiving unit;

a preliminary data determining unit which is used for obtaining or optimizing the space movement data of the virtual marker points according to the relative position relationship and the second set of data received by the calibration data receiving unit;

a data conversion and outputting unit which is used for constructing and outputting three-dimensional and six-degrees-of-freedom movement data of the left and right knee joints according to the displacement of the space movement data of the virtual marker points along the anatomical coordinate system of the joint and the rotation around the anatomical coordinate system of the joint.

Due to the above technical solutions, the present invention has the following beneficial effects compared to the prior art: actual marker points are set around the joint, and the number and distribution of the actual marker points are determined according to the bony structure of the joint, and the space position of the distribution can track the space movement of the bony structure of the joint, and provides a space position reference for the positional changes of the bony structure of the joint; because the actual marker points are captured by the optical tracking devices, the data captured by the optical tracking device form the space movement data of the actual marker points, and can track the movement of the joints. After the date collection device collecting the space movement data of the actual marker points, the data is optimized through the data analyzing device to obtain the movement data of the virtual points, and then obtain the movement of joints. The analysis method can realize dynamic analysis during the joint movement, and can ensure the best test position of the joint in a small space, and can ensure the stability of the data during the test.

DESCRIPTION OF THE DRAWINGS

FIG. 3 is a schematic drawing of detecting marker points by a lens;

FIG. 4 is a schematic flowchart of a knee joint dynamic evaluation method of an embodiment of the present invention;

MODEL OF CARRYING OUT THE INVENTION

In order to make the above objects, features, and advantages of the present invention more apparent, the specific embodiments of the present invention are described in detail below with reference to the accompanying drawings.

In the following description, numerous specific details are set forth in order to provide a thorough understanding of the present invention. However, the present invention can be implemented in many other manners different from those described herein, and those skilled in the art can make similar extensions without departing from the essence of the present invention. Therefore, the present invention is not limited by the specific embodiments disclosed below.

The joint movement analysis system of the present invention can objectively and dynamically analyze the joint movement condition, and the established simulation data can truly track the joint movement condition. When used in the clinic, it can provide a judgment basis for the diagnosis of joint diseases, and can provide quantitative data comparison for evaluating the effect of joint treatment to realize digitalization, individualization, precision, and big data of joint diagnosis and treatment. However, the joint movement analysis system of the present invention is not only suitable for clinical joint diagnosis, but also can be used in other occasions where joint analysis is required, such as physical joint analysis and joint function assessment in rehabilitation, and can also be used in bionics as the basis for making robots or other devices.

When the joint motion analysis method of the present invention is applied to the diagnosis of human joint diseases, it cannot directly obtain the diagnosis result of the joint disease, but merely simulates the joint motion. Of course, the joint motion analysis method of the present invention can also be used in other applications.

Figure 1:
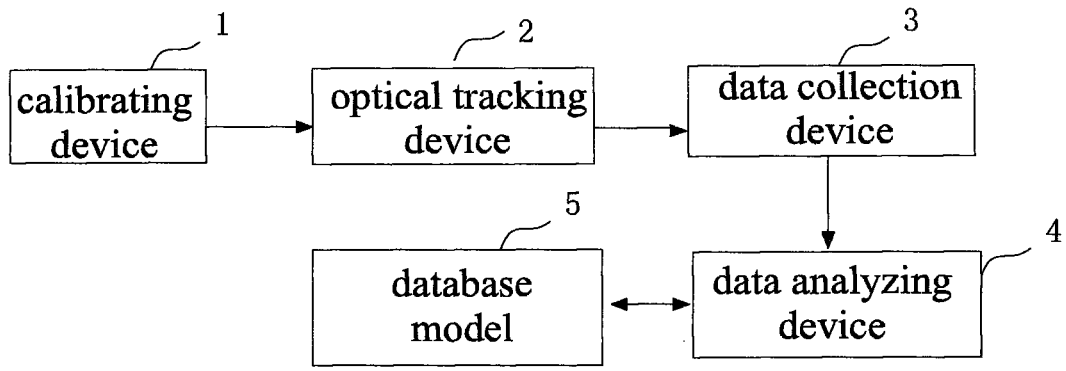
FIG. 1 is a structural block diagram of a joint movement analysis system of an embodiment of the present invention.

Referring to FIG. 1, in one embodiment, a joint movement analysis system includes a calibrating device 1, an optical tracking device 2, a data collection device 3, and a data analyzing device 4. Wherein, the calibrating device 1 is disposed around the joints of the human body and realizes the movement analysis of the body joints. The optical tracking device 2 and the calibrating device 1 communicate with each other through light sensing. The optical tracking device 2 continuously senses each actual marker points, thereby forming space movement data according to dynamic changes. The data collection device 3 is connected with the optical tracking device 2 on the one hand so as to collecting space movement data of the optical tracking device 2, and on the other hand, it is connected with the data analyzing device 4, and transmits the collected preprocessed data to the data analyzing device 4 to reconstruction.

Wherein, the calibrating device 1 is used to set actual marker points around the joints and to set virtual marker points at the anatomical bony landmark positions the joint. The space position of the actual marker points can track the space movement of the bony structure of the joint. And establish the space relative position of the virtual marker points and the actual marker points. The actual marker points or virtual marker points may be a smaller calibrating component as long as it can be sensed by the optical tracking device 2.

The space relative position between the virtual marker points and the actual marker points can be calibrated by, for example, a characteristic calibration pointer and the characteristic calibration pointer is used together with the optical tracking device.

The calibrating device 1 is preferably a flexible calibrating device, such as an elastic binding device or a convenient attachment device, which binds or attaches actual marker points to a set position around the joint, which is fast and reliable. By capturing the bony structure movement of the joint through the actual marker points set on the joint surface, the relative movement between the bony structures constituting the joint is calculated and the joint movement is obtained. It can be used for the movement analysis and evaluation of a knee joint, an ankle joint, a hip joint wrist joint, an elbow joint, and a shoulder joint.

The optical tracking device 2 senses the space position of the actual marker points. With the movement of the joint, the space position of the actual marker points also changes, and the optical tracking device 2 captures the change of the space position to obtain the space movement data of the actual marker points. Of course, the optical tracking device 2 also senses the initial space position of the actual marker points.

Preferably, the optical tracking device 2 is an infrared sensing device, and the actual marker point of the calibrating device 1 is an object that can be sensed by the infrared sensing device. The optical tracking device 2 can synchronously acquire a plurality of actual marker points. The position of the optical tracking device is within the effective test range, which ensures that the accrual marker points of the joint can be collected and calibrated in a small space. Compared with the prior art, there is no need to set multiple motion capture cameras. This avoids the problems of cumbersome calibration and large floor space.

Specifically, the optical tracking device 2 may be a dual infrared or multi-infrared integrated optical positioning sensor, which determines the space position of the actual marker points by the time difference between infrared light emission and reflection or the time difference of infrared light reception, the time difference between infrared light emission and reception so as to obtain the spatial motion data.

The data collection device 3 is used to collect the space movement data of the actual marker points sensed by the optical tracking device and the relative position data of the virtual marker points and the actual marker points. The virtual marker points, for example, are also collected into the data collection device 3 together with the actual marker points after being calibrated, except that the virtual marker points are set on the anatomical bony landmark positions of the joint, and the virtual marker points are set at the corresponding typical characteristic point through the calibrating device, also through sensing and collecting method to form its relative space position with the actual marker points, the space position of the initial virtual marker points is fixed. According to space position changes of the actual marker points, the space movement data updates the virtual marker points by optimization, and results a dynamically change, and tracks the actual joint movement. Because the space position relationship of the actual marker points and the virtual marker points remains substantially unchanged or only changes negligibly, once the space relationship is established, a space movement data of the virtual marker points can be obtained by only analysis of the space movement date of the actual marker points.

According to an embodiment, under the condition that the geometric relationship between the actual marker points and the virtual marker points remains substantially unchanged or changes negligibly during the joint movement, the data collection device 3 obtains the space movement data of the virtual marker points by optimization operation of the space movement data of the actual marker points, to obtain a movement data of the joint.

According to an embodiment, the calibrating device includes at least two actual marking element groups used for marking the actual marker points, each actual marking element group comprises at least four marking elements. The relative position between the marking elements is substantially unchanged or changes negligibly during the joint movement. The optical tracking device senses the marking elements so as to determine the space position data of the actual marker points.

Optionally, the calibrating device further includes at least one set of specific marking element groups for marking the virtual marker points; the optical tracking device senses all actual marking element groups and all specific marking element groups simultaneously at least one time to determine the relative position of the actual marker points and virtual marker points. Specifically, the optical tracking device can measure the physical marking elements (specific marking element groups), and then determine the position of the virtual marker points by the positional relationship between the physical marking elements and the desired virtual marker points. The position relationship between the specific marking element groups and the virtual marker points can be configured, and one or more virtual marker points can be configured according to requirement. This method can prevent the limitation that a calibrator cannot be placed or blocked due to the position of the virtual marker points, and can improve the position accuracy of the virtual marker points. After the optical tracking device senses the actual marking element groups and the specific marking element groups simultaneously, the geometric relationship between the actual marker points and the virtual marker points can be determined. In the subsequent movement process, the geometric relation is basically unchanged or changes negligibly, such that the space movement data of the virtual marker points can be determined by sensing the space movement data of the actual marker points.

After the geometric relationship between the actual marker points and the virtual marker points is established, when the movement of the virtual marker points is determined by the actual marker points, a marker point deviation may occur during the operation of the calibrating device or the human body movement. If there are four or more marking elements that mark the actual marker points, and in an initial state the spacing between any two actual marker points is determined according to the four actual marker points that are sensed, during the following operations, any three of the four actual marker points are sorted so that the actual marker points selected in any frame can correspond to the actual marker points of the initial frame. If the relative position between the actual marker points and the virtual marker points is unchanged during the joint movement, the position of the virtual marker points can be directly determined. If there is a slight change, the distance between the virtual marker points and the actual marker points of the arbitrary frame after sorted is closest to the distance between the virtual marker points and the actual marker points of the initial frame, so the space position of the virtual marker points can be determined through optimization. In other words, according to the characteristic that the distance between any three marking elements for marking the actual marker points in the actual marking element groups and the calibrated virtual marker points remains unchanged or changes negligibly in the knee joint movement, it is a optimization object that the distance between the virtual marker points and the said three actual marker points is closest to the distance between the virtual marker points and the said three actual marker points in initial position in the process that the optical tracking device sensing and obtaining any frame of the joint movement, thus to determine the space position of the virtual marker points, and obtain the space movement data of the virtual marker points.

The data analyzing device 4 is used for performing optimization calculations to obtain space movement data of the virtual marker points, and simulating and analyzing the movement of the bony structure of the joint according to the space movement data of the virtual marker points. The simulation analysis result can be further displayed through a graphical interface, and thus can intuitively observe the joint movement, and facilitates a further analysis.

In one embodiment, the data analyzing device 4 simulates and analyzes the three-dimensional six-degree-of-freedom (6DOF) movement data of the joint according to the displacement of the space movement data of the virtual marker points along the anatomical coordinate system of the joint and the rotation around the anatomical coordinate system of the joint. Based on this, the real motion characteristics of the joints are characterized and the results of the tests can objectively, quantitatively and accurately track the actual condition of the joints.

The joint movement analysis system of the present invention can make the joint analysis no longer be a static image, but can track the actual motion of the joint through dynamic images and curves, and the analysis result is not a subjective judgment or a qualitative assessment, but can objectively and quantitatively track the actual movement of the joint.

As a further embodiment, the joint movement analysis system also includes a database module 5 which stores normal human joint movement data; the data analyzing device 4 is also used to compare the acquired three-dimensional six-degree-of-freedom movement data and that of the normal human joints. The normal person's movement data refers to the joint movement data of the joints that have not been detected or damaged. In the present embodiment, the three-dimensional and six-degree-of-freedom movement data of the joint is also obtained by detecting the actual movement of the human joint. By comparing the three-dimensional six-degree-of-freedom movement data obtained by the detected joint with the normal human joint movement data, measure abnormalities in the joints during exercise can be obtained, so as to diagnose joint diseases quickly and accurately.

The space movement data of the actual marker points, the space movement of the virtual marker points, and the analysis result data may also be stored in the database module 5 and can be retrieved for use.

The joint movement analysis system of the present invention can integrate the data collection device 3 and the data analyzing device 4 and related equipment into one, and is configured as a movable platform so that it can provide the best test location for joints.

Figure 2:
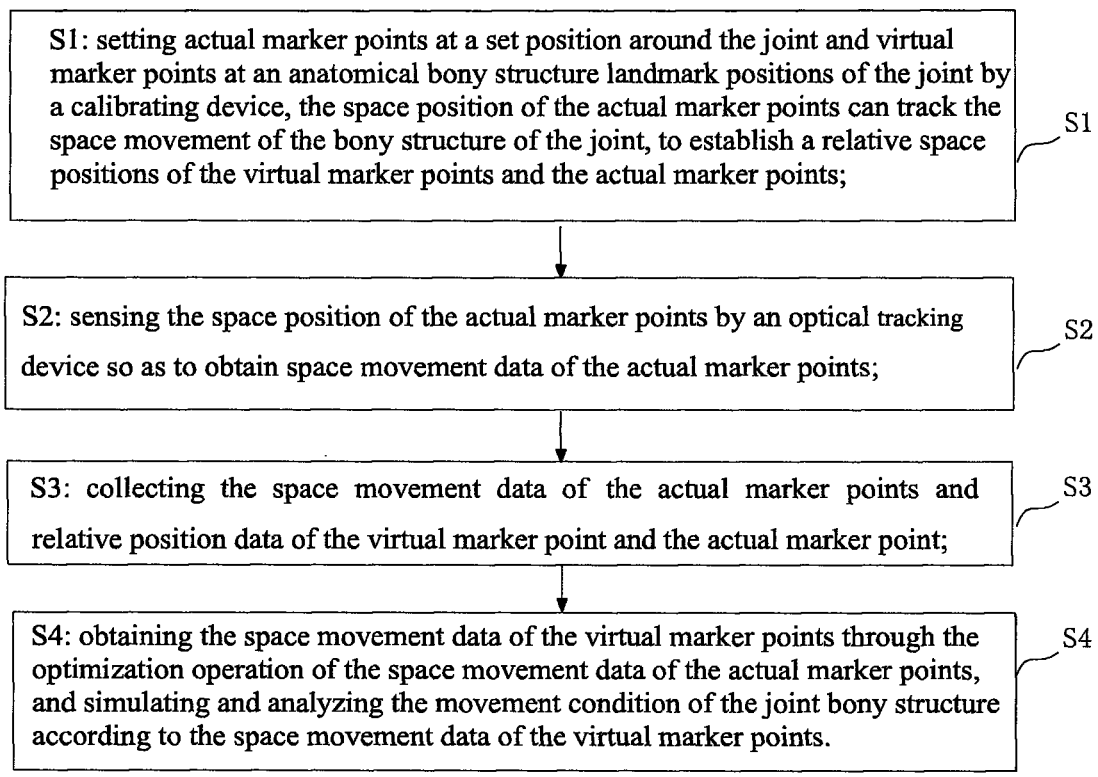
FIG. 2 is a schematic flowchart of a joint movement analysis method of an embodiment of the present invention.

As shown in FIG. 2, the present invention further provides a joint movement analysis method comprising the following steps:

S1: setting an actual marker points at a set position around the joint and virtual marker points at anatomical bony landmark positions of the joint by a calibrating device. The space position of the actual marker points can track the space movement of the bony structure of the joint, and establish the relative space positions of the virtual marker points and the actual marker points;

S2: sensing the space position of the actual marker points by an optical tracking device so as to obtain space movement data of the actual marker points;

S3: collecting the space movement data of the actual marker points and obtaining the space movement data of the virtual marker points through the optimization operation of the space movement data of the actual marker points.

S4: simulating and analyzing the movement condition of the joint bony structure according to the space movement data of the virtual marker points.

The joint movement analysis method of the present invention can be realized by the joint movement analysis device according to the embodiments said above. According to an embodiment of the present invention, the said calibrating device includes at least two actual marking element groups used for marking the actual marker points. Each actual marking element group comprises at least four marking elements. The relative position between the marking elements remains substantially unchanged or changes negligibly during the joint movement. Alternatively, the said calibrating device includes at least one set of special marking element group used for marking the virtual marker points. The said optical tracking device can sense all of the actual marking element groups and the special marking element groups synchronously at least one time so as to determine the relative space position of the actual marker points and the virtual marker points.

Preferably, in the step S3, according to the characteristic that the distance from any three marking elements used for marking the actual marker points to the virtual marker points which has been marked remains substantially unchanged or changes negligibly during the joint movement, the data analyzing device determines the space position of the virtual marker points selected in any frame of joint movement sensed by the optical tracking device according to the object that the distance from the virtual marker points to the three actual marker points is approach the distance from the said virtual to the three actual marker points in original position, and obtains the space movement data of the virtual marker points.

In the step S3, the space movement data of the virtual marker points is obtained by optimization operation of the space movement data of the actual marker points under the condition that the geometric relationship between the actual marker points and the virtual marker points remains substantially unchanged or changes negligibly during the joint movement.

Further more, a step S5 is further included after the step S4, in this step, simulating and analyzing the three-dimensional and six-degree-of-freedom movement data of the joint according to the displacement of the space movement data of the virtual marker points along the anatomical coordinate system of the joint and the rotation around the anatomical coordinate system of the joint.

In the step S2, the space position of the actual marker points are determined by at least two optical positioning sensors (or be called lens) according to the time difference between light emission and reflection or the time difference of light reception so as to obtain the space movement data of the actual marker points; the relative space position of the virtual marker points and the actual marker points is established by sensing the space position of the actual and virtual points at least one time.

As shown in FIG. 3, only two marker points 103, 104 and two lens 101,102 are shown. In fact, more marker points and lens can be included. The marking elements corresponding to the marker points can actively track and passively track. The lens can emit or receive light. In normal station, lens 101 and 102 simultaneously emit and simultaneously receive reflection light 106 and 106 which are tracked respectively by the marker points 103 and 104, and form two different 2D imagine 109 and 110. The position of the marker points in three dimensional space can be calculated through trigonometric function according to the distance of the two lens 101 and 102 and the connecting line of the position of the lens and marker points in their respective imagine. The marker points may be marker points formed by the marking elements corresponding to the actual marker points or to the virtual marker points, or maybe the virtual marker points.

When catch the optical marker points by two or more lens, a false point may be formed according to optical principle in some station. Continue refer to FIG. 3, when the connecting lint from marker points 103 to 104 is parallel to the connecting lint from lens 101 to 102, i.e. the four points is in a same plane, the two lens can receive reflection light 8 of different marker points. Then, the connecting line from two lens to marker points can form a false marker point 105 in space. In fact, the false marker point 105 needs to be filtered. The filtering method is as follow: first, calculate the quantity of the collected marker points, if it is equal to the specified quantity, the false point need not to be filtered; if it is more than the specified quantity, filter the false point. Set or input the minimum distance (a), maximum distance (b); for each point collected (p1, p2, . . . , pn), calculate the minimum distance (a1, a2, . . . , an), maximum distance (b1, b2, . . . , bn) with other point, if it is less than minimum distance (a) or more than the maximum distance (b), the point is judged to be a false point, and need to be filtered.

In the step 2, calculating the distance from each marker point to other marker points for each frame of imagine, and sorting the distance; comparing the back frame with the front frame, to search for each marker point based on minimum distance errors, and making marker points in the back frame corresponding to that in the front frame. Specifically, catching the marker points by at least two lens, indicating each marker point of the first frame by serial number (p1, p2, . . . pn), and calculating distance from each point pm to other points of this frame and sorting the distance from small to big (pm1, pm2, . . . pmn). Calculating distance from each point qm of subsequent frame to other points in this frame and sorting the distance from small to big (qm1, qm2, . . . qmn). Comparing the sorting distance of a marker point in subsequent frame with the sorting distance of all marker points in the first frame, the most approach of accumulated distance difference is selected to obtain a corresponding point in the first frame of any point and a number is provided to the point corresponding to the initial first frame, so as to track the position change of the marker points to obtain the space movement of the marker points.

For the specific content of the joint motion analysis method, please refer to the foregoing description of the joint motion analysis system, which will not be described here again. It should be noted that the analysis result obtained by the joint motion analysis method is only the motion result of the joint, not the diagnosis result.

As shown in FIG. 3, the knee joint dynamic evaluation method of the embodiment includes the following steps:

T1: constructing an evaluation model which includes at least a first angular difference threshold $\alpha 1$ and a second angular difference threshold $\alpha 2$ for determining the movement angular difference, and an anterior-posterior displacement difference threshold $\varepsilon$ for determining the anterior-posterior displacement movement difference, and a grading system according to these thresholds;

T2: synchronously collecting a single set of three-dimensional and six-degree-of-freedom motion data of the left knee joint and that of the right knee joint, each set of three-dimensional and six-degree-of-freedom movement data includes at least a flexion/extension angle, a medial and lateral tilt angle, and a medial and lateral rotation angle and anterior-posterior displacement movement values;

T3: comparing the three-dimensional and six-degree-of-freedom movement data of the left and right knee joints, and calculating the differences of the flexion and extension angle, the medial and lateral tilt angles, the medial and lateral rotation angles, and the anterior-posterior displacement movement values;

T4: inputting the differences into the evaluation model to obtain a corresponding grading system; if all three angular differences are smaller than the first angular difference threshold $\alpha 1$ and the difference of anterior-posterior displacement movement value is smaller than the anterior-posterior displacement difference threshold $\varepsilon$, then the evaluation model outputs a first evaluation level; if at least one angular difference is within the closed interval formed by the first angular difference threshold $\alpha 1$ and the second angular difference threshold $\alpha 2$, and the difference of the anterior-posterior displacement movement value is smaller than the anterior-posterior displacement difference threshold $\varepsilon$, then the evaluation model outputs a second evaluation level; if at least one angular difference is greater than or equal to the second angular difference threshold $\alpha 2$ and the difference of anterior-posterior displacement movement value is smaller than the anterior-posterior displacement difference threshold $\varepsilon$, or all three angular differences are smaller than the second angular difference threshold $\alpha 2$ and the difference of the anterior-posterior displacement movement value is greater than or equal to the anterior-posterior displacement difference threshold $\varepsilon$, the evaluation model outputs a third evaluation level; if at least two angular differences are greater than or equal to the second angular difference threshold $\alpha 2$, or at least one angular difference is greater than or equal to the second angular difference threshold $\alpha 2$ and the difference of anterior-posterior displacement movement value is greater than or equal to the anterior-posterior displacement difference threshold $\varepsilon$, then the evaluation model outputs a fourth evaluation level.

The following is a detailed description of each step of the knee Dynamic evaluation method.

First, step T1 is performed to construct an evaluation model. In order to obtain the knee joint movement state, the evaluation model needs to solve the evaluation results corresponding to the three-dimensional six-degree-of-freedom movement data. The evaluation model includes at least a first angular difference threshold $\alpha 1$ and a second angular difference threshold $\alpha 2$ for determining the movement angular difference, and an anterior-posterior displacement difference threshold $\varepsilon$ for determining the anterior-posterior displacement movement difference value, and a grading system according to the thresholds; each threshold can be used as an endpoint to form different numerical ranges. When the processed three-dimensional six-degree-of-freedom movement data falls into the different numerical ranges, different results of grading system are obtained correspondingly. The results of grading system can objectively track the movement of the knee joints.

Taking the first angular difference threshold α1, the second angular difference threshold α2 and the anterior-posterior displacement difference threshold ε as evaluation criteria can quantitatively track the degree of movement of the knee joint, so that the three-dimensional six-degree-of-freedom movement data can be divided into different grade, and obtain the grading system.

In a preferred embodiment, the first angular difference threshold α1 may be in a range of 3 to 7 degrees, and the second angular difference threshold α2 may be in a range of 8 to 12 degrees. The displacement difference threshold ε may be in the range of 1 to 2 cm. More preferably, the first angular difference threshold α1 is 5 degrees, the second angular difference threshold α2 is 10 degrees, and the anterior-posterior displacement difference threshold ε is 1.5 cm.

Selecting the first angular difference threshold α1, the second angular difference threshold α2 and the anterior-posterior displacement difference threshold ε in the foregoing embodiment can make the grading system match the evaluation result obtained by the internationally authoritative lysholm score questionnaire to the greatest extent. Compared with the lysholm score questionnaire, the method of the present invention does not require the subject to fill in the questionnaire according to the motion perception, the operation method is more simple, and is not influenced by subjective factors of the subject.

Next, step T2 is performed to simultaneously acquire three-dimensional and six-degrees-of-freedom data of both knee joints during the movement of the left and right knee joints. Wherein, At least and preferably, the flexion and extension angles, the medial and lateral tilt angles, the medial and lateral rotation angles, and the anterior-posterior displacement movement values are regarded as the evaluation data. The remaining data of the three-dimensional and six-degrees-of-freedom data have little influence on the evaluation of the exercise status. In order to avoid adding redundant calculations, key data are selected for evaluation.

Figure 5:
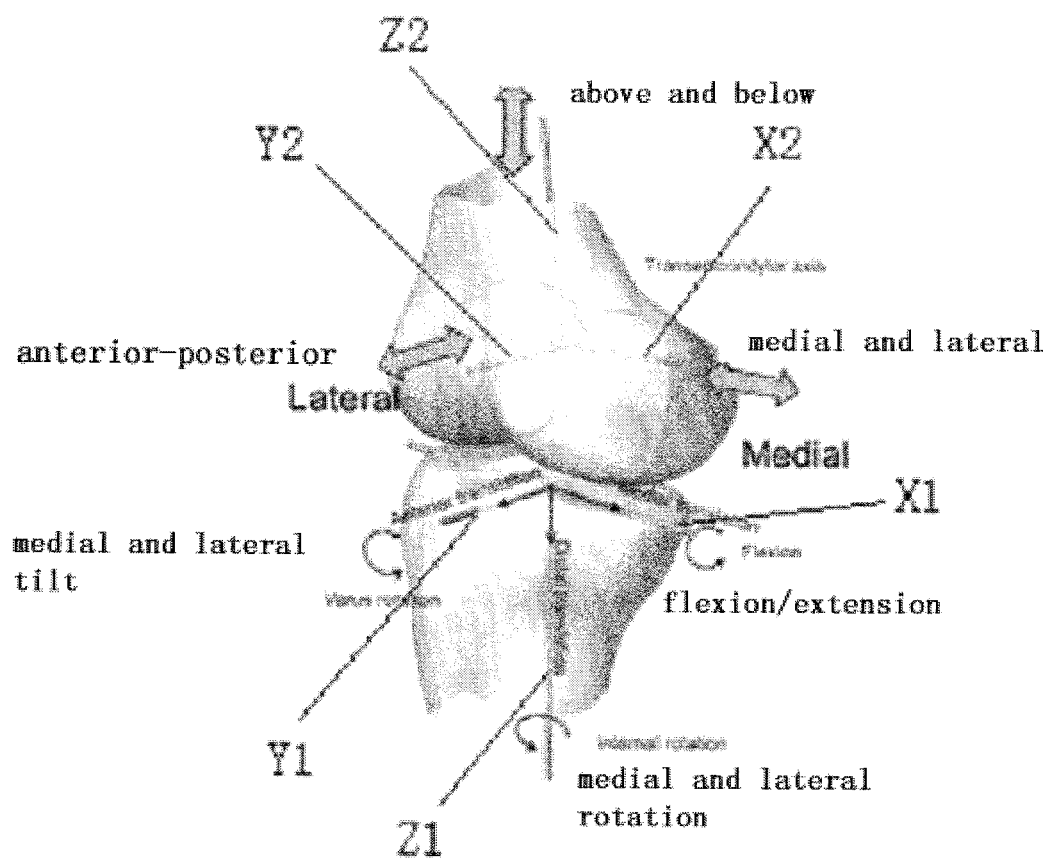
FIG. 5 is a schematic diagram of a three-dimensional six-degree-of-freedom movement of a knee joint of an embodiment of the present invention.

Referring to FIG. 5, a knee joint is located in a three-dimensional and six-degree-of-freedom coordinate system (X1, Y1, Z1, X2, Y2, Z2). In the movement state, the flexion-extension angle refers to the total rotation angle that the upper and lower bones of the right and left knee joints rotates respectively relative to the X1 and X2 axes. The medial and lateral tilt angles refer to the total rotation angle that the upper and lower bones of the right and left knee joints rotates respectively relative to the Y1 and Y2 axes. The medial and lateral rotation angles refer to the difference of rotation angles that the upper and lower bones of the right and left knee joints rotates respectively relative to the Z1 and Z2 axes. The anterior-posterior displacement movement difference value refers to the values of the displacement movement distance between the left and right bones when the upper and lower bones move in the Y1 and Y2 directions respectively.

Simultaneous acquisition of three-dimensional and six-degrees-of-freedom data of both knee joints can only collect a single set of data. Preferably, in step T2, the three-dimensional six-degree-of-freedom movement data is collected synchronously for the left knee joint and the right knee joint in a certain period of time, and the three-dimensional six-degree-of-freedom movement data is collected in multiple cycles. After statistics of the multiple-cycle collected three-dimensional six-degree-of-freedom movement data, a single set of three-dimensional six-degree-of-freedom movement data of the left knee and the right knee are obtained. Statistical methods, for example, are mathematical statistics methods such as making sums, taking mean values, and making variances.

Figure 6:
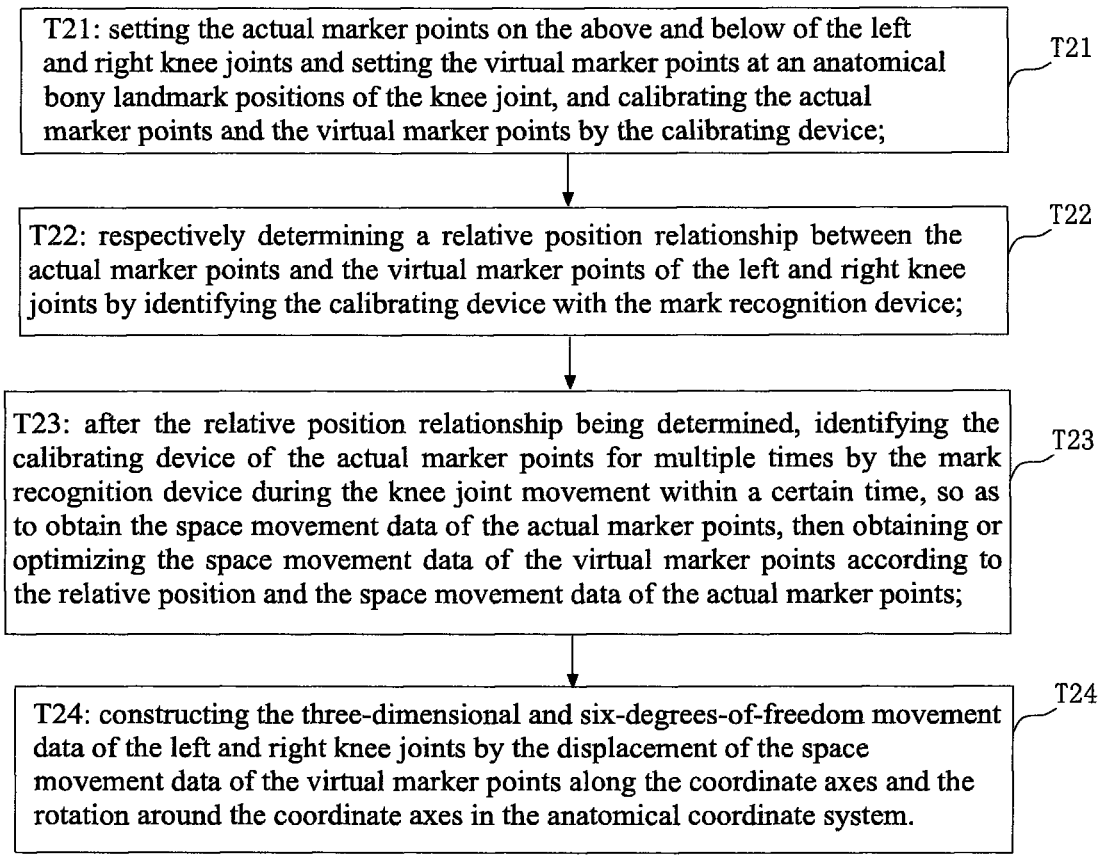
FIG. 6 is a schematic flowchart of a step of collecting three-dimensional six-degree-of-freedom movement data of an embodiment of the present invention.

Furthermore, as shown in FIG. 6, the step of collecting three-dimensional six-degree-of-freedom movement data includes the following steps:

T21: setting the actual marker points above and below the left and right knee joints and setting the virtual marker points at anatomical bony landmark positions of the knee joint, and calibrating the actual marker points and the virtual marker points by the calibrating device.

T22: respectively determining a relative position relationship between the actual marker points and the virtual marker points of the left and right knee joints by identifying the calibrating device with the mark recognition device, T23: after the relative position relationship being determined, identifying the mark position of the actual marker points for multiple times by the mark recognition device during the knee joint movement within a certain time, so as to obtain the space movement data of the actual marker points, then obtaining or optimizing the space movement data of the virtual point according to the relative position and the space movement data of the actual marker points.

T24: constructing the three-dimensional and six-degrees-of-freedom movement data of the left and right knee joints by the displacement of the space movement data of the virtual marker points along the anatomical coordinate system of the joint and the rotation around the anatomical coordinate system of the joint.

The mark recognition device can be an optical tracking device, such as a dual infrared or multi-infrared integrated optical positioning sensor. The calibrating device can be identified and located by the dual infrared or multiple infrared integrated optical positioning sensors so as to determine the position of the actual marker points and the virtual marker points.

In one embodiment, the calibrating device includes at least two actual marking element groups used for calibrating the actual marker points; each actual marking element group comprises at least four marking elements; The relative position of the marking elements remains substantially unchanged or changes negligibly during the knee joint movement. The optical tracking device determines the space position date of the actual marker points by sensing and measuring the marking elements.

Optionally, the calibrating device further includes at least one set of specific marking elements for marking the virtual marker points; the optical tracking device senses all actual marking element groups and all specific marking element groups simultaneously at least one time to determine relative position relationship of the actual marker points and virtual marker points. Specifically, the optical tracking device can measure the physical marking elements (the specific marking element groups), and then determine the position of the virtual marker points by the positional relationship between the physical marking elements and the desired virtual marker points. The position relationship between the specific marking element groups and the virtual marker points can be configured, and one or more virtual marker points can be configured according to requirement. This method can prevent the limitation of not being sensed and measured that the calibrator cannot be placed or blocked due to the position of the virtual marker points, and can improve the position accuracy of the virtual marker points. After the optical tracking device senses the actual marking element groups and the specific marking element groups simultaneously, the geometric relationship between the actual marker points and the virtual marker points can be determined. In the subsequent motion process, the geometric relation remains basically unchanged or changes negligibly, such that the space movement data of the virtual marker points can be determined by sensing the space movement data of the actual marker points.

After the geometric relationship between the actual marker points and the virtual marker points is established, when the movement of the virtual marker points is determined by the actual marker points, a marker point deviation may occur during the operation of the calibrating device or the human body movement. If there are four or more marking elements that mark the actual marker points, and the initial four points are used to determine the spacing between any two actual marker points according to the four actual marker points that are sensed, during the following operations, any three of the four actual marker points are sorted so that the actual marker points selected in any frame can correspond to the actual marker points of the initial frame. If the relative position between the actual marker points and the virtual marker points is unchanged during the joint movement, the position of the virtual marker points can be directly determined. If there is a slight change, the distance between the virtual marker points and the actual marker points after the arbitrary frame sorting is closest to the distance between the virtual marker points and the actual marker points of the initial frame, so the space position of the virtual marker points can be determined through optimization. In other words, according to the characteristic that the distance between any three marking elements in the actual marking element groups of the actual marker points and the calibrated virtual marker points remains unchanged or changes negligibly in the knee joint motion, in any frame of the movement of the joint, the distance between the virtual marker points and the said three actual marker points is closest to the distance between the virtual marker points and the said three actual marker points in initial position. Use this as an optimization goal to determine the space position of the virtual marker points, and obtain the space movement data of the virtual marker points.

Then, step T3 is performed to compare the three-dimensional and six-degree-of-freedom movement data of the left and right knee joints, and to calculate the differences between the two sets of data regarding the flexion and extension angle, the medial and lateral tilt angles, the medial and lateral rotation angles, and the anterior-posterior displacement movement values. In the three-dimensional and six-degrees-of-freedom movement data of the left and right knee joints collected synchronously, the flexion/extension angle, the medial and lateral tilt angle, the medial and lateral rotation angle, and the anterior-posterior displacement movement values respectively correspond to the difference, and obtain the difference data of left and right knee joints, then take the difference data as input parameters of the evaluation model to evaluate.

Finally, step T4 is performed, and the difference data is input into the evaluation model to obtain a corresponding grading system; if all three angular differences are smaller than the first angular difference threshold $\alpha 1$ and the difference of the anterior-posterior displacement movement value is smaller than the anterior-posterior displacement difference threshold $\varepsilon$, then the evaluation model outputs a first evaluation level; if at least one angular difference is within the closed interval formed by the first angular difference threshold $\alpha 1$ and the second angular difference threshold $\alpha 2$, and the difference of the anterior-posterior displacement movement value is smaller than the anterior-posterior displacement difference threshold $\varepsilon$, then the evaluation model outputs a second evaluation level; if at least one angular difference is greater than or equal to the second angular difference threshold $\alpha 2$ and the difference of the anterior-posterior displacement movement value is smaller than the anterior-posterior displacement difference threshold $\varepsilon$, or all three angular differences are smaller than the second angular difference threshold $\alpha 2$ and the difference of the anterior-posterior displacement movement value is greater than or equal to the anterior-posterior displacement difference threshold $\varepsilon$, the evaluation model outputs a third evaluation level; if at least two angular differences are greater than or equal to the second angular difference threshold $\alpha 2$, or at least one angular difference is greater than or equal to the second angular difference threshold $\alpha 2$ and the difference of the anterior-posterior displacement movement value is greater than or equal to the anterior-posterior displacement difference threshold $\varepsilon$, then the evaluation model outputs a fourth evaluation level.

The first evaluation level, the second evaluation level, the third evaluation level, and the fourth evaluation level respectively track the different degrees of movement of the knee joint, and are obtained by collecting the three-dimensional six-degree-of-freedom movement data of the knee joint. The data is more objective and effective, and dynamic assessment can be performed during the movement of the knee joint, with high repeatability and more stable assessment results.

The present invention further provides a knee joint dynamic assessment system, comprising: a model constructing module which is used for constructing an evaluation model, the said evaluation model includes at least a first angular difference threshold $\alpha 1$ and a second angular difference threshold $\alpha 2$ for determining the movement angular difference, and an anterior-posterior displacement difference threshold $\varepsilon$ for determining the anterior-posterior displacement movement difference, and a grading system according to these thresholds;

a data collection module which is used for synchronously collecting a single set of three-dimensional and six-degree-of-freedom motion data of the left knee joint and that of the right knee joint, each set of three-dimensional and six-degree-of-freedom movement data includes at least a flexion/extension angle, a medial and lateral tilt angle, and a medial and lateral rotation angle and anterior-posterior displacement movement values;

a comparison module which is used for comparing the three-dimensional and six-degree-of-freedom movement data of the left and right knee joints and calculating the difference between the flexion and extension angles, the medial and lateral tilt angles, and the medial and lateral rotation angles, and the anterior-posterior displacement movement values in the two sets of data;

a classification output module which is used for obtaining the evaluation model and inputting the difference into the evaluation model to obtain a corresponding evaluation ranking result; if all three angular differences are smaller than the first angular difference threshold $\alpha 1$ and the difference of the anterior-posterior displacement movement value is smaller than the threshold the anterior-posterior displacement difference threshold $\varepsilon$, then the evaluation model outputs a first evaluation level; if at least one angular difference is within the closed interval formed by the first angular difference threshold $\alpha 1$ and the second angular difference threshold $\alpha 2$, and the difference of the anterior-posterior displacement movement value is smaller than the anterior-posterior displacement difference threshold $\varepsilon$, then the evaluation model outputs a second evaluation level; if at least one angular difference is greater than or equal to the second angular difference threshold α2 and the difference of the anterior-posterior displacement movement value is smaller than ε, or all three angular differences are smaller than the second angular difference threshold α2 and the difference of the anterior-posterior displacement movement value is greater than or equal to the anterior-posterior displacement difference threshold ε, the evaluation model outputs a third evaluation level; if at least two angular differences are greater than or equal to the second angular difference threshold α2, or at least one angular difference is greater than or equal to the second angular difference threshold α2 and the difference of the anterior-posterior displacement movement value is greater than or equal to the anterior-posterior displacement difference threshold ε, then the evaluation model outputs a fourth evaluation level.

According to an embodiment of the present invention, setting the actual marker points above and below the left and right knee joints and setting the virtual marker points at anatomical bony landmark positions the knee joint, and calibrating the actual marker points and the virtual marker points by the calibrating device; the data collection module includes:

a calibration data receiving unit which is used for receiving the first set of data obtained by the mark recognition device identifying all calibrating devices, or the second set of data obtained by the mark recognition device multiply identifying the calibrating devices for actual marker points during the knee joint movement;

a position relationship establishing unit which is used for determining a relative position relationship between the actual marker points and the virtual marker points of the left and right knee joints according to the first set of data received by the calibration data receiving unit;

a preliminary data determining unit which is used for obtaining or optimizing the space movement data of the virtual marker points according to the relative position relationship and the second set of data received by the calibration data receiving unit;

a data conversion and outputting unit which is used for constructing and outputting three-dimensional and six-degrees-of-freedom movement data of the left and right knee joints according to the displacement of the space movement data of the virtual marker points along the anatomical coordinate system of the joint and the rotation around the anatomical coordinate system of the joint.

For other specific contents of the knee joint dynamic assessment system, please refer to the foregoing description of the knee joint dynamic evaluation method, which will not be described here again. It should be noted that the evaluation result obtained by the knee joint dynamic assessment system is only the knee joint movement degree but not a diagnosis result.

Although the present invention is disclosed in the preferred embodiments as above, it is not intended to limit the claims, and any person skilled in the art can make possible changes and modifications without departing from the spirit and scope of the present invention. Therefore, the protection scope of the present invention should be subject to the scope defined by the claims.

The invention claimed is:

1. A knee joint dynamic evaluation method for diagnosing human joint diseases by tracking motions of the knee joint, comprising:

T1: constructing an evaluation model which includes at least a first angular difference threshold α1 and a second angular difference threshold α2 for determining angular movement differences, an anterior-posterior displacement difference threshold ε for determining an anterior-posterior displacement movement difference, and a grading system according to these thresholds;

T2: synchronously collecting a single set of three-dimensional and six-degree-of-freedom movement data of a left knee joint and that of a right knee joint with a calibrating device, an optical tracking device and a data collection device, each set of three-dimensional and six-degree-of-freedom movement data includes at least a flexion/extension angle, a medial and lateral tilt angle, a medial and lateral rotation angle and an anterior-posterior displacement movement value, wherein the calibrating device is configured to set actual marker points at a set position around the joint and set virtual marker points at anatomical bony landmark positions of the joint, a space position of the actual marker points is configured to track a space movement of a bony structure of the joint, and to establish a relative space position of the virtual marker points and the actual marker points, the optical tracking device is configured to sense the space position of the actual marker points so as to obtain a space movement data of the actual marker points, the data collection device is configured to collect the space movement data of the actual marker points sensed by the optical tracking device and a relative space position data of the virtual marker points with respect to the actual marker points, wherein the calibrating device is an elastic binding device or a convenient attachment device, which binds or attaches the actual marker points to a set position around the joint, wherein the optical tracking device is an infrared sensing device, a dual infrared or multi-infrared integrated optical positioning sensor;

T3: comparing the three-dimensional and six-degree-of-freedom movement data between the left and right knee joints with a data analyzing device, and calculating differences of the flexion and extension angles, the medial and lateral tilt angles, the medial and lateral rotation angles, and the anterior-posterior displacement movement values of the two sets of movement data, wherein the data analyzing device is configured to obtain a space movement data of the virtual marker points by optimization operating of the space movement data of the actual marker points, simulate and analyze a movement condition of the bony structure of the joint according to the space movement data of the virtual marker points;

T4: inputting the differences into the evaluation model to obtain the corresponding grading system; if the differences of the three angles are all smaller than the first angular difference threshold α1 and the difference of the anterior-posterior displacement movement value is smaller than the anterior-posterior displacement difference threshold ε, then the evaluation model outputs a first evaluation level; if at least one angular difference is within a closed interval formed by the first angular difference threshold α1 and the second angular difference threshold α2, and the difference of the anterior-posterior displacement movement value is smaller than the anterior-posterior displacement difference threshold ε, then the evaluation model outputs a second evaluation level; if at least one angular difference is greater than or equal to the second angular difference threshold α2 and the difference of the anterior-posterior displacement movement value is smaller than the anterior-posterior displacement difference threshold ε, or the differences of the three angles are all smaller than the second angular difference threshold α2 and the difference of the anterior-posterior displacement movement value are all greater than or equal to the anterior-posterior displacement difference threshold ε, then the evaluation model outputs a third evaluation level; if at least two angular differences are greater than or equal to the second angular difference threshold α2, or at least one angular difference is greater than or equal to the second angular difference threshold α2 and the difference of the anterior-posterior displacement movement value is greater than or equal to the anterior-posterior displacement difference threshold ε, then the evaluation model outputs a fourth evaluation level, wherein the first angular difference threshold α1 is in a range of 3 to 7 degrees, and the second angular difference threshold α2 is in a range of 8 to 12 degrees, the anterior-posterior displacement difference threshold ε is in a range of 1 to 2 cm.

2. The knee joint dynamic evaluation method of claim 1, wherein the first angular difference threshold α1 is 5 degrees, and the second angular difference threshold α2 is 10 degrees, and the anterior-posterior displacement difference threshold ε is 1.5 cm.

3. The knee joint dynamic evaluation method of claim 1, wherein, step T2 comprises respectively and synchronously multi-cycle collecting the three-dimensional and six-degree-of-freedom movement data of the left and right knee joint in a certain period of time, obtaining the single set of three-dimensional and six-degree-of-freedom movement data of the left knee and the single set of three-dimensional and six-degree-of-freedom movement data of the right knee by numerical statistics of the multi-cycle collected three-dimensional and six-degree-of-freedom movement data, where the numerical statistics comprises making sums, taking mean values, and making variances.

4. The knee joint dynamic evaluation method of claim 1, wherein a step of collecting the three-dimensional and six-degree-of-freedom movement data includes the following steps:
   T21: setting actual marker points above and below the left and right knee joints and setting virtual marker points at anatomical bony landmark positions of the knee joint, and calibrating the actual marker points and the virtual marker points by a calibrating device;
   T22: respectively determining a relative position relationship between the actual marker points and the virtual marker points of the left and right knee joints by identifying the calibrating device with a mark recognition device;
   T23: after the relative position relationship being determined, identifying the calibrating device of the actual marker points for multiple times by the mark recognition device during a knee joint movement within a certain time, so as to obtain a space movement data of the actual marker points, then obtaining or optimizing a space movement data of the virtual marker points according to the relative position relationship and the space movement data of the actual marker points. T24: constructing the three-dimensional and six-degrees-of-freedom movement data of the left and right knee joints by displacement of the space movement data of the virtual marker points along an anatomical coordinate system of the joints and a rotation around the anatomical coordinate system of the joints.

5. The knee joint dynamic evaluation method of claim 4, wherein the calibrating device includes at least two actual marking element groups used for calibrating the actual marker points; each actual marking element group comprises at least four marking elements;
   a relative position of the marking elements remains substantially unchanged or changes negligibly during the knee joint movement.

6. The knee joint dynamic evaluation method of claim 5, wherein the calibrating device includes at least one set of special marking element group used for marking the virtual marker points; in the step T22, the mark recognition device can synchronously sense all of the actual marking element groups and the special marking element groups at least in one time so as to determine the relative position relationship of the actual marker points and the virtual marker points.

7. The knee joint dynamic evaluation method of claim 6, wherein, in the step T23, according to the characteristic that a distance from any three marking elements used for marking the actual marker points to the virtual marker points which has been marked remains substantially unchanged or changes negligibly during the knee joint movement, the mark recognition device determines the space position of the virtual marker points selected in any frame of knee joint movement sensed by the mark recognition device according to the object of optimization that the distance from the virtual marker points to three actual marker points is approach the distance from the virtual marker points to the three actual marker points in original positions, and obtains the space movement data of the virtual marker points.

8. A knee joint dynamic assessment system for diagnosing human joint diseases by tracking motions of the knee joint, comprising:
   a model constructing module configured for constructing an evaluation model, the evaluation model includes at least a first angular difference threshold α1 and a second angular difference threshold α2 for determining a movement angular difference, and an anterior-posterior displacement difference threshold ε for determining an anterior-posterior displacement movement difference, and a grading system according to these thresholds;
   a data collection module configured for synchronously collecting a single set of three-dimensional and six-degree-of-freedom movement data of the left knee joint and that of the right knee joint, each set of three-dimensional and six-degree-of-freedom movement data includes at least a flexion/extension angle, a medial and lateral tilt angle, and a medial and lateral rotation angle and an anterior-posterior displacement movement value;
   a comparison module configured for comparing the three-dimensional and six-degree-of-freedom movement data of the left and right knee joints and calculating differences of the flexion and extension angles, the medial and lateral tilt angles, the medial and lateral rotation angles, and the anterior-posterior displacement movement values of the two sets of movement data;
   a classification output module configured for obtaining the evaluation model and inputting the differences into the evaluation model to obtain a corresponding assessing grade result; if the differences of three angle are all smaller than the first angular difference threshold α1 and the difference of the anterior-posterior displacement movement value is smaller than the anterior-posterior displacement difference threshold ε, then the evaluation model outputs a first evaluation level; if at least one angular difference is within the closed interval formed by the first angular difference threshold $\alpha 1$ and the second angular difference threshold $\alpha 2$, and the difference of the anterior-posterior displacement movement value is smaller than the anterior-posterior displacement difference threshold $\varepsilon$, then the evaluation model outputs a second evaluation level; if at least one angular difference is greater than or equal to the second angular difference threshold $\alpha 2$ and the difference of the anterior-posterior displacement movement value is smaller than the anterior-posterior displacement difference threshold $\varepsilon$, or differences of the three angle are all smaller than the second angular difference threshold $\alpha 2$ and the difference of the anterior-posterior displacement movement value is greater than or equal to the anterior-posterior displacement difference threshold $\varepsilon$, then the evaluation model outputs a third evaluation level; if at least two angular differences are greater than or equal to the second angular difference threshold $\alpha 2$, or at least one angular difference is greater than or equal to the second angular difference threshold $\alpha 2$ and the difference of the anterior-posterior displacement movement value is greater than or equal to the anterior-posterior displacement difference threshold $\varepsilon$, then the evaluation model outputs a fourth evaluation level, wherein the first angular difference threshold $\alpha 1$ is in a range of 3 to 7 degrees, and the second angular difference threshold $\alpha 2$ is in a range of 8 to 12 degrees, the anterior-posterior displacement difference threshold $\varepsilon$ is in a range of 1 to 2 cm.

9. The knee joint dynamic assessment system according to claim 8, wherein, setting actual marker points above and below left and right knee joints and setting virtual marker points at anatomical bony landmark positions of the knee joint, and calibrating the actual marker points and the virtual marker points by a calibrating device; the data collection module includes:

a calibration data receiving unit configured for receiving a first set of data obtained by a mark recognition device identifying all calibrating devices, or a second set of data obtained by the mark recognition device identifying the calibrating devices for the actual marker points during the knee joint movement for multiple-times;

a position relationship establishing unit configured for determining a relative position relationship between the actual marker points and the virtual marker points of the left and right knee joints according to the first set of data received by the calibration data receiving unit;

a preliminary data determining unit configured for obtaining or optimizing the space movement data of the virtual marker points according to the relative position relationship and the second set of data received by the calibration data receiving unit;

a data conversion and outputting unit configured for constructing and outputting the three-dimensional and six-degrees-of-freedom movement data of the left and right knee joints according to the displacement of the space movement data of the virtual marker points along an anatomical coordinate system of the joint and the rotation around the anatomical coordinate system of the joint.

* * * * *